United States Patent [19]

Majeti

[11] 4,098,881
[45] Jul. 4, 1978

[54] COMPOSITIONS TO CONTROL THE CHRONIC EFFECTS OF EXPOSURE TO SUNLIGHT COMPRISING CONJUGATED DIENES

[75] Inventor: Satyanarayana Majeti, Cincinnati, Ohio

[73] Assignee: The Procter & Gamble Company, Cincinnati, Ohio

[21] Appl. No.: 625,800

[22] Filed: Oct. 28, 1975

Related U.S. Application Data

[63] Continuation-in-part of Ser. No. 544,432, Jan. 27, 1975, abandoned.

[51] Int. Cl.² ............................................. A61K 7/44
[52] U.S. Cl. .................................... 424/59; 424/60; 424/174
[58] Field of Search .............. 424/59, 60, 174, 337, 424/320, 355, 361, 83, 263, 273, 269, 356, 310, 305

[56] References Cited

U.S. PATENT DOCUMENTS

| | | | |
|---|---|---|---|
| 2,134,947 | 11/1938 | Isermann | 424/59 |
| 2,276,204 | 3/1942 | Kilgore | 424/59 X |
| 2,312,715 | 3/1943 | Holmes et al. | 424/83 |
| 2,377,188 | 5/1945 | Schwenk | 424/60 X |
| 3,256,312 | 6/1966 | Strobel et al. | 424/59 X |
| 3,272,713 | 9/1966 | Runge | 424/59 |
| 3,275,520 | 9/1966 | Strobel et al. | 424/59 |
| 3,336,357 | 8/1967 | Strobel et al. | 424/59 X |
| 3,764,537 | 10/1973 | Macleod | 424/83 |

Primary Examiner—Dale R. Ore
Attorney, Agent, or Firm—Walter L. Stumpf; Jerry J. Yetter; Richard C. Witte

[57] ABSTRACT

Compositions and a method for controlling the chronic effects of prolonged exposure to sunlight utilizing conjugated dienes in combination with a topical skin compatible surfactant containing carrier.

2 Claims, No Drawings

COMPOSITIONS TO CONTROL THE CHRONIC EFFECTS OF EXPOSURE TO SUNLIGHT COMPRISING CONJUGATED DIENES

This application is a continuation-in-part of application Ser. No. 544,432, filed Jan. 27, 1975 now abandoned.

BACKGROUND OF THE INVENTION

The present invention relates to cosmetic compositions comprising select conjugated dienes, which, when topically applied to animal, including human, skin provide protection from the chronic effects of prolonged exposure to sunlight.

A variety of physiological responses to ultraviolet radiation have been observed, and various methods of controlling the harmful responses have been provided. The most well recognized responses include, for example, immediate responses such as the generation of erythema (sunburn) followed by reversible pigmentation or melanization, and chronic responses such as wrinkling, creasing, and carcinoma of the skin. In general, it is believed that both immediate and chronic responses occur as a consequence of varying degrees of exposure to ultraviolet radiation in the range of 2950A to 4000A. Within this range, ultraviolet radiation is able to penetrate the outer protective layers of the skin.

One means of controlling undesirable responses to ultraviolet radiation is to avoid exposure to sunlight for more than short periods of time. However, most people enjoy outdoor recreation and admire melanization of the skin. Moreover, some degree of insolation is desirable to insure adequate Vitamin D synthesis. Accordingly, previous research has focused on methods of controlling the more immediate erythemogenic responses, thus enabling people to enjoy exposure without undue discomfort or irritation. Commercially available "suntanning" preparations mitigate the dosage of erythemogenic radiation which penetrates the outer skin thereby allowing the tanning response while preventing severe erythema. A wide variety of ultraviolet reflecting and absorbing agents are known and disclosed in the prior art.

Although suntanning preparations enable people to enjoy outdoor activities without discomfort, such preparations also mute the natural warning system which calls attention to the prospect of chronic damage. As a consequence of the prolonged periods of exposure, encouraged by reduced erythemogenic response, absorbed ultraviolet radiation is believed to cause chronic changes in the epidermis. Hyperkertinization, which constitutes the major natural defense to prolonged exposure; increased marking of the skin; areas of pigmentation and atrophy; superficial scaling and telangiectasis or tumorous swelling of the small blood vessels constitute some of the visible signs of chronic damage. The development of skin cancer or pre-cancerous lesions (actinic keratoses) is also known to be induced by extensive exposure to erythemogenic radiation.

Accordingly, while known compositions comprising sunscreening and ultraviolet radiation absorbing agents provide relief from the more immediate erythemogenic response, the chronic effects of prolonged exposure to sunlight remain substantially unaffected.

SUMMARY OF THE INVENTION

The present invention provides cosmetic compositions which, when topically applied, provide substantially complete relief from the chronic effects of exposure to sunlight, comprising from about 0.001% to about 25% by weight of a select conjugated diene in combination with a topical pharmaceutically acceptable surfactant containing vehicle.

DETAILED DESCRIPTION OF THE INVENTION

The essence of the instant invention resides in the discovery that certain conjugated dienes, more thoroughly described hereinafter, when topically applied prevent the undesirable chronic effects of prolonged exposure to sunlight. Cosmetic compositions comprising these conjugated dienes can be topically applied to prevent chronic damage to the skin without inhibiting the desirable responses to insolation.

The select conjugated dienes suitable for use in the compositions of this invention are those capable of quenching the excited-states of biogenic chromophores contained in aromatic amino and nucleic acids. Although not wishing to be bound by theory, it is believed that undesirable cell change resulting from exposure to sunlight can be controlled by inhibiting one or more of the usual photochemical reactions that affect DNA and RNA syntheses. One of the known photochemical reactions that influences DNA and RNA syntheses is the photodimerization of pyrimidine bases, thymine and cytosine in the case of DNA, and uracil and cytosine in the case of RNA. Photodimerization reactions can be broadly described as the Photocyclo-addition of a ground-state molecule with an excited-state molecule. Certain conjugated dienes are known excited-state quenchers, see, for example, Lamola, *Pure Appl. Chem.* 34, No. 2, (1973), "Photochemistry and Structure in Nucleic Acids". Thus, it has been found that by utilizing conjugated dienes to quench the excited-state of the biogenic chromophores, it is possible to inhibit photodimerization of the bases and consequently control undesirable cellular change, i.e., chronic damage.

The class of conjugated dienes capable of quenching the excited-state of biologic chromophores can be generically described by the following formulae:

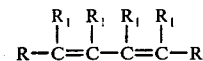

wherein each R is $-(Ch_2)_nR_2$ wherein $R_2$ is hydrogen, hydroxyl, amine, amide, carboxyl, carboxamide, methoxyl, etherically linked sugar, sulfur heteroatom, or $-C(O)OR_3$ wherein $R_3$ is hydrogen, lower alkyl, methoxyl, hydroxyl, amine, amide, carboxyl, or phenyl and wherein $n$ is an integer from 1 to about 10; and wherein the ends of the diene chain may combine to form a cyclic diene of the formula

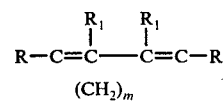

wherein $m$ is an integer from 1 to about 10; and wherein each $R_1$ is hydrogen, lower alkyl, or $-(CH_2)_nR_2$ wherein $R_2$ is as defined above and $n$ is as defined above.

The conjugated dienes suitable for use herein are staple items of commerce available from a variety of chemical manufacturers. In general, conjugated dienes can be synthesized by the acid-catalyzed dehydration of diols. A detailed description of the synthesis of conjugated dienes can be found at Chapter 34 of *The Chemistry of Organic Compounds*, Noller (ed.), W. B. Saunders Company, 1966.

Conjugated dienes suitable for use in this invention include, for example, (A) Sulfoxides such as:
4-(1-cyclohexenyl)-3-butenyl methyl sulfoxide,
3,5-hexadienyl octyl sulfoxide,
3,5-hexadienyl phenyl sulfoxide,
3-ethylidene-4-hexenyl octyl sulfoxide, and
3-ethylidene-4-hexenyl phenyl sulfoxide;

(B) Sulfones such as:
4-(1-cyclohexenyl)-3-butenyl lower alkyl sulfones,
3,5-hexadienyl lower alkyl sulfones,
3,5-hexadienyl phenyl sulfone,
3-ethylidene-4-hexenyl lower alkyl sulfones, and
3-ethylidene-4-hexenyl phenyl sulfone;

(C) Sulfinyls such as:
1,8-bis (methyl sulfinyl)-3,5-octadiene,
1-(2-lower alkyl sulfinyl-1-ethyl)-1,3-cyclo $C_6$ to $C_8$ conjugated dienes,
2-(2-lower alkyl sulfinyl-1-ethyl)-1,3-cyclo $C_6$ to $C_8$ conjugated dienes,
6-(2-methyl sulfinyl-1-ethyl)-1,3-cyclo hexadiene,
6-(2-methyl sulfinyl-1-ethyl)-1,3-cyclo heptadiene,
2-(2-lower alkyl sulfinyl-1-ethyl)-3-(2-hydroxy-1-ethyl)-1,3-cyclo $C_6$ to $C_{10}$ conjugated dienes, and
7-(methyl sulfinyl methyl) cholesta-3,5-diene;

(D) Sulfonyls such as:
1,8-bis (lower alkyl sulfonyl)-3,5-octadiene,
2-(2-lower alkyl sulfonyl-1-ethyl)-1,3-cyclo $C_6$ to $C_8$ conjugated dienes,
6-(2-lower alkyl sulfonyl-1ethyl)-1,3-cyclo $C_6$ to $C_8$ conjugated dienes, and
2-(2-lower alkyl sulfonyl-1-ethyl)-3(2-hydroxy-1-ethyl)-1,3-cyclo $C_6$ to $C_{10}$ conjugated dienes;

(E) Amines such as:
2,4hexadien-1-amine,
1,6-diamino-2,4-hexadiene,
2-lower alkyl amino-1,3-butadienes,
1-amino-3,5-heptadiene,
1-amino-3,5-hexadiene,
1,8-diamino-3,5-octadiene,
3-methylene-4-hexene-1-amine,
3-(1-amino-2-ethyl)-2,4-hexadiene,
1-amino-4,6-dodecadiene,
1-di lower alkyl amino-3,5-hexadienes,
1,9-bis(di-lower alkyl amino)-4,6-nonadiene,
1-di-methyl amino-3-methylene-4-hexane,
1-N-phenyl-N-lower alkyl amino-3,5-hexadienes,
1-N-piperidino-3,5-hexadiene,
1-lower alkyl amino-3,5-heptadienes,
1,2-dihydropyridine,
3-vinyl-1,2,5,6-tetrahydropyridine,
2,7-dihydroazepine,
2,3,8,9-tetrahydroazonine,
4-(1-hydroxy-3-butenyl)-1,2,5,6-tetrahydropyridine,
2,3,8,9-tetrahydro-N-lower alkyl azonines,
1-(2-amino-1-ethyl)-1,3-cyclononadiene,
2-(2-amino-1-ethyl)-1,3-cyclononadiene,
1-(2-di-lower alkyl amino-1-ethyl)-1,3-cyclononadienes,
1,4-bis(2-di-methyl amino-1-ethyl)-1,3cyclononadiene,
1-(2-piperidino-1-ethyl)-1,3-cyclononadiene;

(F) Hydrocarbons such as:
2,3,4,5-tetramethyl-2,4-hexadiene,
1,3-decadiene,
2,2,7,7-tetramethyl-3,5-octadiene,
5,6-dimethylene decane,
1,3-eicosadiene,
1,3-cyclohexadiene,
1,3-cycloheptadiene,
1,3-cyclooctadiene,
1,3-cyclononadiene,
1,3-cyclohexadecadiene,
1-butyl-1,3-cyclodecadiene,
2-butyl-1,3-cyclodecadiene,
1-(8-octa-2,4-dienyl)-1,3-cyclononadiene,
1-vinylcyclohexene,
1-vinylcycloheptene,
1,1'-bis cyclohexene, and
hexalin;

(G) Alcohols such as:
2,4-hexadien-1-ol,
3,5-heptadien-1-ol,
3,5-octadien-1,8-diol,
3-methylene-4-penten-1-ol,
3-ethylidene-4-hexen-1-ol,
6,7-bis(1-hydroxy-2-ethyl)-5,7-dodecadiene,
3-(1-hydroxy-2-ethyl)-1,8-dihydroxy-3,5-octadiene,
9,11-dodecadien-1-ol,
octa-5,7-dien-1,2-diol,
4,6-heptadien-2-ol,
2,9-dihydroxy-2-methyl-4,6-nonadiene,
2,9-dihydroxy-4,6-decadiene,
5-hydroxymethyl-1,3-cyclohexadiene,
2-(1-hydroxy-2-ethyl)-1,3-cyclohexadiene,
2,3-bis(1-hydroxy-2-ethyl)-1,3-cyclohexadiene,
2-(1-hydroxy-2-ethyl)-1,4-dimethyl-3-butyl-1,3-cyclohexadiene,
1-(1-hydroxy-2-ethyl)-1,3-cycloheptadiene,
2-(1-hydroxy-2-ethyl)-1,3-cycloheptadiene,
2,6-bis(1-hydroxy-2-ethyl)-1,3-cycloheptadiene,
6-(1-hydroxy-2-ethyl)-1,3-cycloheptadiene,
1-(1-hydroxy-2-ethyl)-cyclonona-1,3-diene,
7-hydroxy-1,3-cyclononadiene,
7-(1-hydroxy-2-ethyl)-1,3-cyclononadiene,
1-(1-hydroxy-2-ethyl)-1,3-cyclotetradecadiene,
2-(1-hydroxy-2-ethyl)-$\Delta^{1(2),8}$-hexalin,
$\Delta^{1(2),8}$-6-hexalol, and
1,1'-bis cyclohexene-4-ol;

(H) Ethers such as:
7-ethoxy-1,3-heptadiene,
1-ethoxy-2,4-hexadiene,
1,6-diethoxy-2,4-hexadiene,
4-(2-ethoxy-1-ethyl)-3,5-heptadien-1-ol,
6-glucosyl-1-hepta-2,4-dienyl ether,
1-glucosyl-1-hepta-2,4-dienyl ether, and
4,5-dioxo, $\Delta^{1,8}$-hexalin;

(I) Carboxyls such as:
3,5-hexadienoic acid,
3,5-octadien-1,8-dioic acid,
5,7-nonadienoic acid,
4,6-decadiene-1,10-dioic acid,
5-ethylidene-6-octenoic acid,
4-(2-propenyl)-nona-1,9-dioic acid,
2-carboxy-5,7-nonadienoic acid,
2-methyl-5,7-nonadienoic acid,
2-amino-5,7-nonadienoic acid,
10,12-tridecadienoic acid,
9-hydroxy-4,6-nonadienoic acid,
1-carboxymethyl-1,3-cyclohexadiene,
2,4-cyclohexadienoic acid,
2-carboxymethyl-1,3-cyclohexadiene,
1-(1-carboxy-2-ethyl)-1,3-cyclohexadiene,
2-(1-carboxy-2-ethyl)-6-carboxy-1,3-cyclohexadiene, 1,4-dimethyl-2-(1-carboxy-2-ethyl)-1,3-cyclohexadiene
2-(1-carboxy-3-propyl)-3-(1-hydroxy-2-ethyl)-1,3-cyclohexadiene,
1-(1-carboxy-2-ethyl)-1,3-cycloheptadiene,
6-(1-carboxy-2-ethyl)-1,3-cycloheptadiene,
3,5-cycloheptadienoic acid,
2,4-cyclodecadienoic acid,
4,6-cyclononadienoic acid,
1-(1-carboxy-2-ethyl)-1,3-cyclotetradecadiene,
$\Delta^{1(2),8}$-hexalin-6-carboxylic acid, and
7-(1carboxy-2-ethyl)-$\Delta^{1(2),8}$-hexalin;

(J) Amides, phenyl amides, and N-lower alkyl amides of the above carboxylic acids;

(K) Lower alkyl esters of the above carboxylic acids; and (L) Polyol esters of the above carboxylic acids prepared by the reaction of the above acids and polyols such as sugars and lower alkanols. Sugars suitable for use in the formation of the sugar esters of the invention include monosaccharides and disaccharides. Examples of suitable monosaccharides include those carbohydrates which do not hydrolyze such as glucose, mannose, galactose, arabinose, xylose, ribose, apitose, rhamnose, fucose, psicose, fructose, sorbose, tagitose, ribulose, zylose, and erythrulose. Examples of suitable disaccharides include those carbohydrates which yield only a few molecules of monosaccharides on hydrolysis such as maltose, kojibiose, nigerose, cellobiose, lactose, mellbose, gentiobose, turanose, rutinose, tremalose, sucrose, and raffinose. It should be noted that suitable sugars are characterized by a plurality of hydroxyl groups which may be converted to ether linkages. For present purposes, the ether linkage can be formed from any of the available hydroxyl groups located within the sugar structure without altering the effectiveness of the diene itself. Thus, the present invention contemplates the use of conjugated dienes, as defined above, having an etherically linked sugar moiety without regard to the location of the ether linkage relative to the sugar moiety per se.

As used hereinbove, the term "lower alkyl" is intended to include $C_1$ to $C_{10}$ alkyl, for example, methyl, ethyl, propyl, butyl, octyl, and decyl.

Preferred conjugated dienes suitable for use herein include, for example, sulfoxides such as 3,5-hexadienyl octyl sulfoxide; 3,5-hexadienyl phenyl sulfoxide; and 3-ethylidene-4-hexenyl octyl sulfoxide; sulfinyls such as 1,8-bis (methyl sulfinyl)-3,5-octadiene, 6-(2-methyl sulfinyl-1-ethyl)-1,3-cyclo hexadiene, 6-(2-methyl sulfinyl-1-ethyl)-1,3-cyclo heptadiene, and 7-(methyl sulfinyl methyl) cholesta-3,5-diene; amines such as 1-amino-3,5-heptadiene, 1,8-diamino-3,5-octadiene, 1-amino-4,6-dodecadiene, di-methyl amino-3-methylene-4-hexene, 1,4-bis(2-di-methyl amino-1-ethyl)-1,3-cyclononadiene, and 1-(2-piperidino-1-ethyl)-1,3-cyclononadiene; hydrocarbons such as 1,3-decadiene, 1,3-cyclononadiene, and 1-(8-octa-2,4-dienyl)-1,3-cyclononadiene; alcohols such as 3,5-heptadien-1-ol, 3,5-octadien-1,8-diol, 3-ethylene-4-hexen-1-ol, 3-(1-hydroxy-2-ethyl)-1,8-dihydroxy-3,5-octadiene, 2,9-dihydroxy-4,6-decadiene, 2,3-bis(1-hydroxy-2-ethyl)-1,3-cycloheptadiene, $\Delta^{1(2),8}$-6-hexalol; ethers such as 1,6-diethoxy-2,4-hexadiene, 4-(2-ethoxy-1-ethyl)-3,5-heptadien-1-ol; and carboxyls such as 3,5-octadien-1,8-dioic acid, 4-(2-propenyl)-nona-1,9-dioic acid, 2-methyl-5,7-nonadienoic acid, 9-hydroxy-4,6-nonadienoic acid, and 2-(1-carboxy-3-propyl)-3-(1-hydroxy-2-ethyl)-1,3-cyclohexadiene.

Especially preferred conjugated dienes suitable for use herein include, for example, 3,5-hexadienyl octyl sulfoxide; 3,5-hexadienyl phenyl sulfoxide; 3-ethylidene-4-hexenyl octyl sulfoxide; 1,8-bis(methyl sulfinyl)-3,5-octadiene; 7-(methyl sulfinyl methyl) cholesta-3,5-diene; 1-amino-3,5-heptadiene; 1,8-diamino-3,5-octadiene; 1-amino-4,6-dodecadiene; 1-(2-piperidino-1-ethyl)-1,3-cyclononadiene; 1,3-decadiene; 2,4-hexadien-1-ol; 1,3-octadien-5-ol; and 1-(8-octa-2,4-dienyl)-1,3-cyclononadiene.

It has been found that suitable conjugated dienes can be structurally tailored to provide not only protection from chronic damage but also protection from more immediate erythemogenic responses by incorporating a sunscreening or ultraviolet radiation absorbing moiety into the basic diene structure. Thus, the present invention encompasses compositions for topical protection from both erythema and chronic damage.

Especially preferred conjugated dienes structurally tailored to provide, as an additional benefit, protection from erythemogenic responses include, for example, esters and amides prepared by reaction of conjugated dieneols and amines, such as those enumerated above, with the acid of an ultraviolet radiation screening or absorbing compound. Specific acids suitable for use in preparing tailored conjugated dienes include, for example, p-methoxy cinnamic acid, p-aminobenzoic acid, salicylic acid, p-dimethyl amino benzoic acid, and uraconic acid.

The compositions of the present invention comprise from about 0.001% to about 25%, preferably 0.01% to 15%, by weight, of a conjugated diene. It has been found that below about 0.001%, by weight, the conjugated dienes do not provide significant protection from the chronic damage of prolonged exposure to ultraviolet radiation; and that concentrations above about 25%, by weight, do not significantly enhance the efficacity of the compositions of this invention.

As noted, the present invention encompasses compositions for topically controlling chronic skin damage comprising a conjugated diene, as described above, and a surfactant-containing vehicle. It has been found that the surface active agent provides a more efficient absorption and retention by the skin of the active ingredient of the compositions of this invention. Various vehicles have been employed to carry the active, and the make-up of the vehicle profoundly affects the efficacy of the product. Suitable vehicles, once spread on the skin, should remain in place as a continuous film, closely adhering to or penetrating the skin surface, and should resist washing off either by perspiration or by immersion in fresh or salt water. The characteristics of a suitable vehicle vary greatly depending essentially upon the ideas and prejudices of the formulator. Creams, cream lotions, oils, gels, hydroalcoholic lotions, jellies, lipsticks and aerosol foams and sprays are common formulations. In any event, suitable vehicles contain from about 0.1% to about 10% of a nonionic, cationic, or amphoteric surface active agent; the preferred amount is in the range of about 0.1% to about 2%. The upper limit of such surface active agent (surfactant) is critical where large amounts may result in excessive foaming. Cationic, and particularly nonionic, surface active agents are desirable although anionic nonsoap surfactants are also suitable. Anionic non-soap surfactants are preferably used at concentrations of about 0.01% to about 0.5% and desirably below about 0.1%.

Water-soluble nonionic surfactants are highly suitable for use in this invention; they include detergent compounds produced by the condensation of alkylene oxide groups (hydrophilic in nature) with an organic hydrophobic compound which may be aliphatic or alkyl aromatic in nature. Examples of such detergents are: the polyalkylene glycol esters, ethers, and thioethers of the types, RCOO(—C$_2$H$_4$O)$_n$—H,
RO(—C$_2$H$_4$O)$_n$—H, and
RS(—C$_2$H$_4$O)$_n$—H wherein R represents long chain alkyl radicals having from about 8 to about 18 carbon atoms and $n$ is an integer from about 4 to about 30; the polyethylene oxide condensates of alkyl phenols, e.g., the condensation products of alkyl phenols having about 6 to 12 carbon atoms in the alkyl group, in either straight chain or branched chain configuration, with ethylene oxide in amounts equal to 10 to 25 moles of ethylene oxide per mole of alkyl phenol; compounds formed by condensing ethylene oxide with a hydrophobic base formed by the condensation of propylene oxide with propylene glycol; the condensation product of ethylene oxide with the product resulting from the reaction of propylene oxide and ethylene diamine. More specific examples of some suitable nonionic detergents are: the reaction products of t-octylphenol with an average of from 9 to 30 moles of ethylene oxide per mole, and the water-soluble waxy reaction products of lauryl alcohol and ethylene oxide having a titer of about 35° C or higher and of oleyl alcohol and ethylene oxide having a titer of about 29° C or higher.

Other examples of nonionic surfactants are: tertiary trialkyl amine oxides wherein one alkyl group contains 10-18 carbon atoms and the other alkyl groups are short chain groups (a specific example is dodecyl dimethyl amine oxide); hexadecyl dimethyl ammonio propionate; 3-(hexadecyl dimethyl ammonio)-propane-1-sulfonate.

The preferred nonionic surfactant is available on the market under the tradename of "Pluronic". These compounds are formed by condensing ethylene oxide with a hydrophobic base formed by the condensation of propylene oxide with propylene glycol. The hydrophobic portion of the molecule exhibits water insolubility. Its molecular weight is of the order of 1500 to 1800. The addition of polyoxyethylene radicals to this hydrophobic portion tends to increase the water solubility of the molecule as a whole. Liquid products are obtained up to the point where the polyethylene content is about 50% of the total weight of the condensation product. Further increase in the relative content of polyoxyethylene to hydrophobic portion renders the final product wax-like or solid in consistency. The molecular weights of Pluronic L-61, L-64 and F-68 which find particular utility in the practice of the present invention are about 2000, 3000 and 8000 respectively.

Examples of cationic surfactants suitable for practice of this invention are the detergent quaternary ammonium salts. Such salts have the general formula:

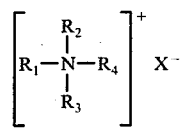

wherein R$_1$ is a hydrophobic radical and R$_2$, R$_3$, and R$_4$ are each hydrocarbon radicals. R$_1$ can be aliphatic, unsaturated aliphatic, cycloaliphatic, acyl, aliphaticaryl and arylaliphatic radicals containing 8 to 25 carbon atoms, e.g., branched or normal chain alkyl phenoxy alkoxy alkyl, branched or long chain alkyl cresoxy alkoxy alkyl, long chain alkoxyaryl, branched or long chain alkyl phenoxy alkyl, long chain alkyl aryl, halogen-substituted long chain alkylaryl, aryl alkyl, long chain alkyl, long chain alkenyl and cycloalkyl. R$_2$, R$_3$, and R$_4$ can contain each 1 to 10 carbon atoms, with the total carbon atoms in the three radicals being from 3 to 12. Examples of R$_2$, R$_3$, and R$_4$ are low molecular weight alkyl, preferably methyl or ethyl, or aryl, preferably phenyl, or arylalkyl, preferably benzyl.

X is a salt forming radical which is an anionic radical capable of forming a water-soluble salt. Chloride and bromide are preferred but halides generally, sulfates, phosphates, methosulfate, and other salt forming ions are also satisfactory.

Examples of amphoteric detergent surfactants are alkyl beta imino dipropionates and alkyl beta amino propionates, wherein the alkyl group contains 10 to 20 carbon atoms, and imidazoline derivatives of the Miranol class. Other examples of amphoteric surfactants may be found in "Surface Active Agents and Detergents, Vol. II", Schwartz, Perry and Berch, pp. 138-143.

Examples of anionic non-soap surfactants suitable for the practice of this invention are the detergents of the sulfonated and sulfated types such as the alkyl (C$_8$-C$_{18}$) sulfates, the alkyl (C$_8$-C$_{18}$) polyethenoxy (1-10 units of —C$_2$H$_4$O—) ether sulfates, the alkyl (C$_8$-C$_{18}$) aromatic sulfonates, the mono- or di-alkyl (C$_8$-C$_{18}$) esters of sulfosuccinic acid, sulfonated or sulfated amides of higher fatty acids, sulfuric acid esters of polyhydric alcohols incompletely esterified with higher fatty acids, higher fatty acids esters of low molecular weight alkylol sulfonic acids, etc., usually in the form of their sodium, potassium, ammonium, or alkanolammonium salts. Some of the particular detergents of this category are: sodium octyl sulfate, sodium nonyl sulfate, sodium decyl sulfate, monethanolammonium dodecyl sulfate, ammonium tetradecyl sulfate, monethanolammonium pentadecyl sulfate, monethanolammonium hexadecyl sulfate, nonoethanolammonium octadecyl sulfate, monoethanolammonium oleyl sulfate, sodium salts of dioctyl sulfosuccinate, sodium octyl benzene sulfonate, sodium nonyl benzene sulfonate, sodium dodecyl benzene sulfonate, sodium tetradecyl benzene sulfonate, ammonium pentadecyl benzene sulfonate, ammonium triisopropyl benzene sulfonate, sodium salts of the oleic acid ester of isethionic acid, sodium salt of the lauric acid amide of taurine, triethanolammonium coconut oil monoglyceride monosulfate, monoethanolammonium tallow diglyceride monosulfate. N lauroyl sarcosinates are also suitable.

In addition to a surfactant, the vehicle used herein may contain solid or liquid diluents, penetrants, thickeners, stabilizers, preservatives, and the like or mixtures thereof.

Diluents which are suitable for use herein include, for example, water, ethanol, glycerin, and saline. Particularly useful diluents are hydrophilic, water-soluble or miscible diluents, which term, for the sake of convenience, is intended to include water itself. Hydrophilic diluents generally lower the freezing point of the diene component so that the compositions are useful at temperatures encountered during cold weather use and storage.

Penetrants which are suitable for use herein include, for example, the dialkyl sulfoxides, and the polyoxyethylene sorbitan higher fatty acid monoesters. U.S. Pat. No. 3,740,420 granted July 19, 1973, describes in detail pharmaceutical penetration and the use of dialkyl sulfoxides as penetrants.

For various applications, the compositions herein may be formulated into convenient form for application with thickening agents. Such forms include thickened solutions or lotions, ointments, creams, gels, and the like. These forms are advantageously employed to lessen the run-off from the skin that may occur with the most fluid composition forms, thereby permitting greater mobility for the user immediately following application. Accidental spilling and undesired contact with the material can also be minimized with these formulations.

It is advantageous to use water dispersible thickening agents (i.e., agents dispersible in water to form a homogeneous distribution or solution), such as polyethylene glycols, as they are readily compatible with water or other diluents and may be readily washed from the skin. Alternatively, an emulsion base may be employed to impart the desired thickening effect, a better spreading and wetting effect, and a retardation of the skin-drying effect of certain penetrants.

The water-soluble thickening bases utilize, for example, a variety of polyethylene glycol having differing viscosities, depending upon the desired consistency; water-dispersible gums; carboxy vinyl polymers, methyl cellulose, alginates, and the like. The compositions incorporating emulsion bases may contain the usual adjuvants such as a fatty alcohol, an emulsifier, and water.

The required application of conjugated diene will vary with the particular circumstances of application, the duration of anticipated exposure, and effectiveness of the carrier component; however, single applications generally range from about 0.25 to about 2 milligrams per square centimeter of epidermal area with up to 4 applications daily. Single applications containing greater than about 2 milligrams per square centimeter are not economical in view of the limited enhanced activity resulting from the additional active present, whereas single applications containing less than about 0.25 milligrams per square centimeter do not have the desired effect.

The skin compatible vehicles employed herein are used at a concentration sufficient to provide a practical topical application. Preferably, the vehicle comprises from about 90% to about 99.9% by weight of a total composition. Suitable vehicle formulations are more thoroughly detailed in Cosmetic Science and Technology, Sagarin (Editor), Interscience Publishers, New York (1957), incorporated herein by reference.

In a preferred embodiment of the invention a suitable conjugated diene and surfactant containing carrier are combined with 1% to 10%, by weight, of a sunscreening or ultraviolet radiation absorbing agent to provide compositions which not only inhibit the chronic damage attributed to prolonged exposure to sunlight but also provide immediate protection from erythema. A wide variety of screening and absorbing agents are suitable for use in combination with the conjugated dienes of this invention. Sagarin, et al. at Chapter VIII, pages 189 et seq., of Cosmetics Science and Technology disclose numerous suitable agents. Specific suitable sunburn preventing agents include, for example, p-Aminoenzoic acid, its salts and its derivatives (ethyl, isobutyl, glyceryl esters; p-dimethylaminobenzoic acid);

Anthranilates (i.e., o-aminobenzoates; methyl, menthyl, phenyl, benzyl, phenylethyl, linalyl, terpinyl, and cyclohexenyl esters);

Salicylates (amyl, phenyl, benzyl, menthyl, glyceryl, and dipropyleneglycol esters);

Cinnamic acid derivatives (menthyl and benzyl esters, α-phenyl cinnamonitrile; butyl cinnamoyl pyruvate);

Dihydroxycinnamic acid derivatives (umbelliferone, methylumbelliferone, methylaceto-umbelliferone);

Trihydroxycinnamic acid derivatives (esculetin, methylesculetin, daphnetin, and the glucosides, esculin and daphnin);

Hydrocarbons (diphenylbutadiene, stilbene);

Dibenzalacetone and benzalacetophenone;

Naphtholsulfonates (sodium salts of 2-naphthol-3,6-disulfonic and of 2-naphthol-6,8-disulfonic acids);

Dihydroxy-naphthoic acid and its salts;

o- and p-Hydroxybiphenyldisulfonates;

Coumarin derivatives (7-hydroxy, 7-methyl, 3-phenyl);

Diazoles (2-acetyl-3-bromoindazole, phenyl benzoxazole, methyl naphthoxazole, various aryl benzothiazoles);

Quinine salts (bisulfate, sulfate, chloride, oleate, and tannate);

Quinoline derivatives (8-hydroxyquinoline salts, 2-phenylquinoline);

Hydroxy or methoxy-substituted benzophenones;

Uric and vilouric acids;

Tannic acid and its derivatives (e.g., hexaethylether);

(Butyl carbityl) (6-propyl piperonyl) ether; and

Hydroquinone.

The following examples are intended to illustrate suitable compositions and methods of their use.

EXAMPLE I

The following solutions were prepared by mechanically blending the recited ingredients in the indicated proportions at room temperature.

| Ingredients | % by weight of Total Composition | | |
|---|---|---|---|
| | A | B | C |
| 2,4-hexadienol | 5% | | |
| 5-hydroxy-1,3-octadiene | | 5% | |
| Ethanol | 72% | 72% | 75% |
| Water | 23% | 23% | 25% |

The clipped backs (approximate area 36 square centimeters) of three groups of twenty Fischer female rats were topically treated with 0.5 milliliter aliquots of Composition A, B, or C. Approximately 3 to 4 hours after application, the animals were exposed to ultraviolet radiation emitted by a bank of four Westinghouse Fluorescent Sunlamps, Model FS-40, for a one-hour period. The period of exposure was calculated as equivalent to three times the minimum erythemal dose. The treatment and exposure were repeated three times a week for twenty-five weeks. The animals were graded every week based upon the degree of visible irritation using a standard scale ranging from 1 to 9.

Repeated exposure to ultraviolet radiation is known to result in irritation varying from erythema to scaling, ulceration, and severe necrosis. The animals treated with Composition C during the exposure period underwent marked changes ultimately reaching an average severity grade of 7.0. In contrast, those animals receiving treatment by either Composition A or B showed only mild to moderate irritation, ultimately reaching an average severity grade of 3.0 in the case of Composition A and 4.8 in the case of Composition B.

EXAMPLE II

The following cream base composition is prepared by conventional methods.

| Ingredients | % by weight of Total Composition |
|---|---|
| 3,5-hexadienyl octyl sulfoxide | 10% |
| Stearic acid | 15% |
| Propylene glycol | 25% |
| Mineral oil | 5% |
| Stearyl alcohol | 1% |
| Polyoxyethylene sorbitan monostearate | 2% |
| Ascorbic acid | 0.5% |
| Sodium bisulfite | 0.25% |
| Water | Balance |

When applied topically, the above composition provides substantially complete protection from the chronic effects of prolonged exposure to ultraviolet radiation.

Additional emollient, cream and lotion compositions are prepared in accordance with the present invention as follows:

| | % by weight of Total Composition EXAMPLE | | | | | | | | |
|---|---|---|---|---|---|---|---|---|---|
| Ingredients | III | IV | V | VI | VII | VIII | IX | X | XI |
| 3,5-hexadienyl phenyl sulfoxide | 8% | — | — | — | — | — | — | — | — |
| 3-ethylidene-4-hexenyl octyl sulfoxide | — | 8% | — | — | — | — | — | — | — |
| 1,8-bis(methyl sulfinyl)-3,5-octadiene | — | — | 9% | — | — | — | — | — | — |
| 7-(methyl sulfinyl methyl)cholesta-3,5-diene | — | — | — | 0.5% | — | — | — | — | — |
| 1-amino-3,5-heptadiene | — | — | — | — | 5% | — | — | — | — |
| 1,8-diamino-3,5-octadiene | — | — | — | — | — | 6% | — | — | — |
| 1-amino-4,6-dodecadiene | — | — | — | — | — | — | 25% | — | — |
| 1-(2-piperadino-1-ethyl)-1,3-cyclononadiene | — | — | — | — | — | — | — | 15% | — |
| 1,3-decadiene | — | — | — | — | — | — | — | — | 12% |
| Beeswax | 5% | — | 12% | 3% | 15% | 5% | — | 6% | — |
| Spermaceti | 3% | — | 4% | 12% | — | — | — | — | 8% |
| Mineral Oil | 30% | — | 23% | — | 15% | 35% | — | — | 20% |
| Decyl methyl sulfoxide | 5% | 1% | — | 15% | — | 2% | 1% | 3% | — |
| Borax | — | — | 1% | 8% | — | — | — | 1% | — |
| Perfume | 1% | 0.5% | 1% | — | 1% | 1% | — | 1% | 1% |
| Lanolin | — | 1% | 1% | 1% | — | 3% | — | — | 1% |
| Methyl cellulose | — | 1% | — | — | 1% | — | — | — | — |
| Ethanol | — | — | — | 1% | 1% | — | 60% | 8% | — |
| Stearic acid | — | 10% | — | — | — | — | — | — | 5% |
| Petrolatum | — | — | — | — | — | 5% | — | 3% | — |
| Water | | | | BALANCE | | | | | |

When topically applied the compositions of the foregoing Examples provide substantially complete protection from the chronic effects of prolonged exposure to ultraviolet radiation.

EXAMPLE XII

The following solution base composition is prepared in accordance with the invention as follows:

| | |
|---|---|
| P-methoxy cinnamic acid ester of 2,4-hexadien-1-ol | 12% |
| Cetyl alcohol | 2% |
| Lanolin | 1% |
| Mineral oil | 2% |
| Polyethylene glycol monostearate | 1% |
| Pectin | 1% |
| Water | Balance |

In the above composition the p-methoxy cinnamic acid ester of 2,4-hexadienol is replaced by the esters of p-amino benzoic acid, salicyclic acid, and p-dimethylamino benzoic acid and 3,5-heptadien-1-ol, 3,5-octadien-1,8-diol, 3-ethylene-4-hexen-1-ol, 3-(1-hydroxy-2-ethyl)-1,8-dihydroxy-3,5-octadiene, 2,9-dihydroxy-4,6-decadiene, 2,3-bis(1-hydroxy-2-ethyl)-1,3-cycloheptadiene, and $\Delta^{1(2)8}$-6-hexalol.

When topically applied the above compositions provide substantially complete protection from the chronic effects of prolonged exposure to sunlight, as well as protection from sunburn.

What is claimed is:

1. A composition adapted for topical application and capable of inhibiting chronic damage to skin induced by ultraviolet radiation in the range of 2,950 A to 4000 A, comprising an effective ultraviolet absorbing amount from about 0.001% to about 25%, by weight, of a conjugated diene ester or amide having an acid portion derived from p-methoxy cinnamic acid, p-aminobenzoic acid, salicylic acid, or p-dimethyl amino benzoic acid, and an alcohol portion derived from:
2,4-hexadien-1-ol,
3,5-heptadien-1-ol,
3,5-octadien-1,8-diol,
3-methylene-4-penten-1-ol,
3-ethylidene-4-hexen-1-ol,
6,7-bis(1-hydroxy-2-ethyl)-5,7-dodecadiene,
3-(1-hydroxy-2-ethyl)-1,8-dihydroxy-3,5-octadiene,
9,11-dodecadien-1-ol,
octa-5,7-dien-1,2-diol,
4,6-heptadien-2-ol,
2,9-dihydroxy-2-methyl-4,6-nonadiene,
2,9-dihydroxy-4,6-decadiene,
5-hydroxymethyl-1,3-cyclohexadiene,
2-(1-hydroxy-2-ethyl)-1,3-cyclohexadiene,
2,3-bis(1-hydroxy-2-ethyl)-1,3-cyclohexadiene,
2-(1-hydroxy-2-ethyl)-1,4-dimethyl-3-butyl-1,3-cyclohexadiene,
1-(1-hydroxy-2-ethyl)-1,3-cycloheptadiene, 2-(1-hydroxy-2-ethyl)-1,3-cycloheptadiene,
2,6-bis(1-hydroxy-2-ethyl)-1,3-cycloheptadiene,
6-(1-hydroxy-2-ethyl)-1,3-cycloheptadiene,
1-(1-hydroxy-2-ethyl)-cyclonona-1,3-diene,
7-hydroxy-1,3-cyclononadiene,
7-(1-hydroxy-2-ethyl)-1,3-cyclononadiene,
1-(1-hydroxy-2-ethyl)-1,3-cyclotetradecadiene,
2-(1-hydroxy-2-ethyl)-$\Delta^{1(2),8}$-hexalin,
$\Delta^{1(2),8}$-6-hexalol, or
1,1'-bis cyclohexene-4-ol;
or an amine portion derived from:
2,4-hexadien-1-amine,
1,6-diamino-2,4-hexadiene,
2-lower alkyl amino-1,3-butadiene,
1-amino-3,5-heptadiene,
1-amino-3,5-hexadiene,
1,8-diamino-3,5-octadiene,
3-methylene-4-hexene-1-amine,
3-(1-amino-2-ethyl)-2,4-hexadiene,
1-amino-4,6-dodecadiene,
1-di lower alkyl amino-3,5-hexadiene,
1,9-bis(di-lower alkyl amino)-4,6-nonadiene,
1-di-methyl amino-3-methylene-4-hexene,
1-N-phenyl-N-lower alkyl amino-3,5-hexdadiene,
1-N-piperidino-3,5-hexadiene,
1-lower alkyl amino-3,5-heptadiene,
1,2-dihydropyridine,
3-vinyl-1,2,5,6-tetrahydropyridine,
2,7-dihydroazepine,
2,3,8,9-tetrahydroazonine,
4-(1-hydroxy-3-butenyl)-1,2,5,6-tetrahydropyridine,
2,3,8,9-tetrahydro-N-lower alkyl azonine,
1-(2-amino-1-ethyl)-1,3-cyclononadiene,
2-(2-amino-1-ethyl)-1,3-cyclononadiene,
1-(2-di-lower alkyl amino-1-ethyl)-1,3-cyclononadiene,
1,4-bis(2-di-methyl amino-1-ethyl)-1,3-cyclononadiene,
or
1-(2-piperidino-1-ethyl)-1,3-cyclononadiene;
in a skin compatible vehicle containing from about 0.1% to about 10%, by weight, surfactant wherein the surfactant is a nonionic, cationic or amphoteric surfactant or from about 0.01% to about 0.5%, by weight, of a non-soap anionic surfactant.

2. A composition adapted for topical application and capable of inhibiting chronic damage to skin induced by ultraviolet radiation in the range of 2,950 A to 4000 A, comprising an effective ultraviolet absorbing amount from about 0.001% to about 25%, by weight of 3,5-hexadienyl octyl sulfoxide, 3,5-hexadienyl phenyl sulfoxide, 3-ethylidene-4-hexenyl octyl sulfoxide, 1,8-bis(-methyl sulfinyl)-3,5-octadiene, 6-(2-methyl sulfinyl-1-ethyl)-1,3-cyclo hexadiene, 6-(2-methyl sulfinyl-1-ethyl)-1,3-cyclo heptadiene, 7-(methyl sulfinyl methyl) cholesta-3,5-diene, 1-amino-3,5-heptadiene, 1,8-diamino-3,5-octadiene, 1-amino-4,6-dodecadiene, di-methyl amino-3-methylene-4-hexene, 1,4-bis(2-di-methyl amino-1-ethyl)-1-3-cyclononadiene, 1-(2-piperidino-1-ethyl)-1,3-cyclononadiene, 1,3-decadiene, 1,3-cyclononadiene, 1-(8-octa-2,4-dienyl)-1,3-cyclononadiene, 2,4-hexadien-1-ol, 3,5-octadien-1,8-diol, 3-ethylene-4-hexene-1-ol, 3-(1-hydroxy-2-ethyl)-1,3-dihydroxy-3,5-octadiene, 2,9-dihydroxy-4,6-decadiene, 2,3-bis(1-hydroxy-2-ethyl)-1,3-cycloheptadiene, $\Delta^{1(2),8}$-6-hexalol, 1,6-diethoxy-2,4-hexadiene, 4-(2-ethoxy-1-ethyl)-3,5-heptadien-1-ol, 3,5-octadien-1,8-dioic acid, 4-(2-propenyl)-nona-1,9-dioic acid, 2-methyl-5,7-nonadienoic acid, 9-hydroxy-4,6-nonadienoic acid, or 2-(1-carboxy-3-propyl)-3-3-(1-hydroxy-2-ethyl)-1,3-cyclohexadiene, in a skin compatible vehicle containing from about 0.1% to about 10%, by weight, surfactant wherein the surfactant is a nonionic, cationic, or amphoteric surfactant or from about 0.01% to about 0.5%, by weight, of a non-soap anionic surfactant.

* * * * *